(12) United States Patent
Mitchell et al.

(10) Patent No.: US 7,833,271 B2
(45) Date of Patent: Nov. 16, 2010

(54) SPINAL IMPLANTS WITH BODY AND INSERT

(75) Inventors: Margaret E. Mitchell, Cedar Park, TX (US); Jim Freid, Round Rock, TX (US)

(73) Assignee: Zimmer Spine, Inc., Minneapolis, MN (US)

( * ) Notice: Subject to any disclaimer, the term of this patent is extended or adjusted under 35 U.S.C. 154(b) by 798 days.

(21) Appl. No.: 10/838,575

(22) Filed: May 4, 2004

(65) Prior Publication Data

US 2005/0251257 A1   Nov. 10, 2005

(51) Int. Cl.
   *A61F 2/44* (2006.01)
(52) U.S. Cl. .................... 623/17.11; 623/17.16
(58) Field of Classification Search .............. 623/17.11, 623/17.16
   See application file for complete search history.

(56) References Cited

U.S. PATENT DOCUMENTS

| | | | | |
|---|---|---|---|---|
| 5,702,449 A | * | 12/1997 | McKay | 623/17.16 |
| 6,126,688 A | * | 10/2000 | McDonnell | 623/17.16 |
| 6,193,756 B1 | * | 2/2001 | Studer et al. | 623/17.15 |
| 6,200,347 B1 | * | 3/2001 | Anderson et al. | 623/16.11 |
| 6,296,664 B1 | * | 10/2001 | Middleton | 623/17.15 |
| 6,607,557 B1 | * | 8/2003 | Brosnahan et al. | 623/17.11 |
| 6,638,310 B2 | * | 10/2003 | Lin et al. | 623/17.11 |
| 6,736,850 B2 | * | 5/2004 | Davis | 623/17.16 |
| 6,783,547 B2 | * | 8/2004 | Castro | 623/17.16 |
| 6,979,353 B2 | * | 12/2005 | Bresina | 623/17.16 |
| 7,238,203 B2 | * | 7/2007 | Bagga et al. | 623/17.11 |

FOREIGN PATENT DOCUMENTS

CA   2 480 884 A1 * 10/2003

* cited by examiner

*Primary Examiner*—David H Willse
*Assistant Examiner*—Javier G Blanco
(74) *Attorney, Agent, or Firm*—Sprinkle IP Law Group

(57) ABSTRACT

A spinal implant is provided which maintains intervertebral spacing and stability within the spine. The spinal implant may include a body and an insert. The body of the spinal implant may be formed of a ceramic material. In some embodiments, the body may be formed of beta tricalcium phosphate. The body may include an opening that is complementary to the insert. The insert may fit within the opening. The insert may include a number of passageways. Some of the passageways may intersect to form a scaffold for bone growth. Bone growth promoting material may be introduced into the insert before the insert is positioned in a body and inserted in a patient between two vertebrae.

20 Claims, 3 Drawing Sheets

SPINAL IMPLANTS WITH BODY AND INSERT

BACKGROUND

1. Field of the Invention

The present invention generally relates to spinal implants. More particularly, certain embodiments of this invention relate to ceramic implants having supportive bodies and bone growth promoting inserts.

2. Description of Related Art

An intervertebral disc may degenerate. Degeneration may be caused by trauma, disease, and/or aging. An intervertebral disc that becomes degenerated may have to be partially or fully removed from a spinal column. Partial or full removal of an intervertebral disc may destabilize the spinal column. Destabilization of a spinal column may result in alteration of a natural separation distance between adjacent vertebrae. Maintaining the natural separation distance between vertebrae may prevent pressure from being applied to nerves that pass between vertebral bodies. Excessive pressure applied to the nerves may cause pain and/or nerve damage. During a spinal fixation procedure, a spinal implant may be inserted within a space created by the removal or partial removal of an intervertebral disc between adjacent vertebrae. The spinal implant may maintain the height of the spine and restore stability to the spine. Bone growth through or around the spinal implant may fuse the adjacent vertebrae.

A spinal implant may be inserted during a spinal fixation procedure using an anterior approach, lateral approach, posterior approach or combination approach. In some situations, an anterior approach may result in an easier approach, less muscle and tissue damage, and less bone removal than other approaches. During some spinal implant insertion procedures, a plate, or bone fastener may be used to augment fusion and/or to inhibit expulsion of the spinal implant.

A discectomy may be performed to remove or partially remove a defective or damaged intervertebral disc. The discectomy creates a disc space for a spinal implant. The amount of removed disc material may correspond to the size and type of spinal implant to be inserted. After a discectomy, a spinal implant may be inserted into the disc space. One or more spinal implants may be inserted between a pair of vertebrae. Spinal implants may be inserted into disc spaces prepared between more than one pair of vertebrae during a spinal fusion procedure.

Spinal surgery may be complex due in part to the proximity of delicate soft tissue such as the spinal cord, cauda equina, and/or vascular structures. Preparation instruments and spinal implants may need to be carefully inserted to avoid damage to soft tissue. Alignment and spacing of a spinal implant that is to be inserted into a patient may be determined before surgery. Achieving the predetermined alignment and spacing during surgery may be important to achieve optimal fusion of adjacent vertebrae.

Bone growth promoting material may be used in conjunction with an implant to facilitate bone growth that will fuse vertebrae together. Bone growth promoting material may include bone. Bone may be autogenic bone, allogenic bone, xenogenic bone or combinations thereof. Autogenic bone is bone obtained from another location of a patient. Allogenic bone is bone derived from the same species as the patient. Xenogenic bone is bone derived from a species other than that of the patient. Bone growth promoting material may include, but is not limited to, bone marrow, calcium phosphates, collagen, calcium sulfates, demineralized bone matrix, bone morphogenetic proteins, and/or platelet derived growth factors. The calcium phosphates may be hydroxapatite, alpha tricalcium phosphate, or beta tricalcium phosphate. Implants may be formed of metal, polymers, ceramics, autogenic bone, allogenic bone, xenogenic bone, or combinations thereof.

SUMMARY

A spinal implant may be used to promote fusion of adjacent vertebrae. The spinal implant may include a body and an insert. The body may be made of a ceramic material such as beta tricalcium phosphate. In some embodiments, the body may be made of metal, polymer, ceramics, or combinations thereof. The body may provide the spinal implant with an ultimate compressive strength that is comparable to the strength of a cortical allograft spacer and stronger than the compressive strength of an intact, un-operated vertebral level. The body may allow for the formation of an implant with a safety factor of three, four, five or greater relative to the strength of an intact, un-operated cervical vertebral level. The body may have a mechanical crush resistance that is greater than the mechanical crush resistance of the insert. The body may include an opening that is sized to accept the insert. The opening and the insert may be sized so that the insert is inhibited from passing completely through the opening.

An insert for a spinal implant may include passageways. In some embodiments, the insert may be formed of a ceramic material (e.g., beta tricalcium phosphate). In some embodiments, the insert may be made of bone (i.e., allograft or xenograft bone). The passageways may facilitate bone ingrowth into the insert when the body, with the insert positioned in the opening of the body, is placed between vertebrae. The passageways may include at least one passageway that extends completely through the insert from top to bottom. The passageways may also include at least one passage that is angled relative to, and intersects with, the passage extending completely through the insert from top to bottom. In some embodiments, the insert may be formed of a porous material.

A spinal implant may be made from a body and an insert. In some embodiments, the body may be made from a block of beta tricalcium phosphate. The periphery of the block may be shaped to conform to a general shape of outer surfaces of a vertebra. In some embodiments, an anterior side of the body may be curved so that the anterior side conforms to the shape of adjacent vertebrae that the spinal implant is to be positioned between. The curve of the anterior side of the spinal implant may be a visual indicator of the posterior and anterior sides of the spinal implant. In some embodiments of spinal implants, the spinal implants may include one or more convex surfaces. In some embodiments of spinal implants, the spinal implants may include one or more concave surfaces. In some embodiments of spinal implants, the spinal implants may include one or more substantially planar surfaces.

In some embodiments, a body may be machined or formed so that the spinal implant has a desired amount of lordotic angle. A top surface and/or a bottom surface of the body may taper such that a height of an anterior side of the spinal implant is greater than a height of a posterior side of the body. In some embodiments, the lordotic angle may be up to about 12° for cervical spinal implants, and up to about 20° for lumbar spinal implants. In some embodiments, the body may not include a lordotic angle. In some embodiments of spinal implants, the spinal implant may include a kyphotic angle (i.e., a height of an anterior side of the spinal implant is less than a height of a posterior side of the spinal implant).

An opening may be formed through the body of a spinal implant. The opening may be sized to complement the insert of the spinal implant. In some embodiments, the opening may be tapered. The taper of the opening may correspond to the taper of a side wall of the insert so that the insert fits in the body. The taper of the opening and the taper of the insert may inhibit passage of the insert through the body.

Bone growth promoting material may be introduced in passageways of an insert. The bone growth promoting material may be, but is not limited to, autologous bone, allograft bone, xenograft bone, calcium phosphates, collagen, calcium sulfates, demineralized bone matrix, bone morphogenetic proteins, platelet derived growth factors, bone marrow aspirate, and/or blood.

A spinal implant may be inserted during a spinal fusion procedure. A discectomy may be performed to establish a disc space between adjacent vertebrae. The vertebrae may be distracted to establish a desired separation distance. Bone growth promoting material may be introduced into passageways of an insert. Solid and/or thick bone growth promoting material may be pressed into the passageways. Liquid bone growth promoting material may be absorbed into the passageways when the insert is soaked in a solution containing the liquid bone growth promoting material. After bone growth promoting material is introduced into the passageways, the insert may be positioned in a body of the spinal implant. The body and insert may be inserted into the disc space. During some spinal fusion procedures, a spinal plate may be attached to the vertebrae after the spinal implant is inserted in the disc space.

BRIEF DESCRIPTION OF THE DRAWINGS

Advantages of the present invention will become apparent to those skilled in the art with the benefit of the following detailed description of embodiments and upon reference to the accompanying drawings in which.

Figure 1:
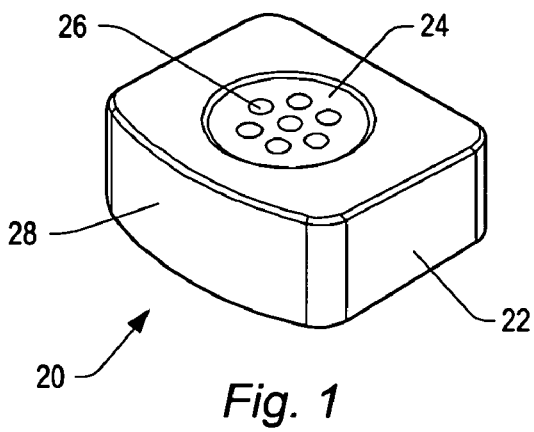
FIG. 1 depicts a perspective view of an embodiment of a spinal implant.

While the invention is susceptible to various modifications and alternative forms, specific embodiments thereof are shown by way of example in the drawings and will herein be described in detail. The drawings may not be to scale. It should be understood that the drawings and detailed description thereto are not intended to limit the invention to the particular form disclosed, but on the contrary, the intention is to cover all modifications, equivalents, and alternatives falling within the spirit and scope of the present invention as defined by the appended claims.

DETAILED DESCRIPTION

A spinal implant may be used during the treatment of trauma, disease, and/or neoplasia. A spinal implant may establish a separation distance between adjacent vertebrae. A spinal implant may fill a defect in a single vertebra. The spinal implant may promote bone growth between the adjacent vertebrae. The bone growth may fuse the vertebrae together. The spinal implant may establish a desired angle between the vertebrae. In some spinal implant embodiments, a surface of the spinal implant that will contact a vertebra, or both surfaces of the spinal implant that will contact the vertebrae, may be tapered so that the spinal implant has a desired angle. A cervical or lumbar spinal implant may have an anterior height that is larger than a posterior height to establish a desired amount of lordosis. A cervical spinal implant may have from about 0° to about 12° of lordotic angle. Some cervical spinal implants may have from about 0° to about 6° of lordotic angle, or from about 3° to about 6° of lordotic angle. A lumbar spinal implant may have between about 0° and about 20° of lordotic angle. In some embodiments, a spinal implant may be formed that will establish a kyphotic angle (i.e., the posterior height of the spinal implant is greater than the anterior height of the spinal implant).

A spinal implant may promote bone growth that fuses adjacent vertebrae together. A spinal implant may promote fusion by a number of mechanisms including osteogenesis, osteoinduction, and/or osteoconduction. Osteogenesis refers to the formation of new bone by cells contained within the spinal implant. Osteoinduction refers to a chemical process where molecules within the spinal implant are converted to material used by the patient to form bone. Osteoconduction refers to a process where a matrix of the spinal implant forms a scaffold on which cells are able to form new bone. A spinal implant or portions of a spinal implant may be formed of material that promotes osteogenesis, osteoinduction, and/or osteoconduction. Initially, the spinal implant may be able to provide structural support to maintain disc height, and as new bone is deposited and remodeled, the spinal implant is absorbed by the body. The absorbed material of the spinal implant may provide material for the formation of new bone. The spinal implant may be formed of a material that is bioabsorbable in a predictable manner.

A spinal implant, or a portion of a spinal implant may be formed of a calcium phosphate compound. One form of a calcium phosphate that may be used to form a spinal implant or a portion of a spinal implant is beta tricalcium phosphate. Beta tricalcium phosphate is classified as a ceramic. The beta tricalcium phosphate used may be over 99% pure beta tricalcium phosphate. One type of beta tricalcium phosphate that may be used for spinal implant applications is Cerasorb®, which is obtainable from Curasan AG (Kleinostheim, Germany).

Beta tricalcium phosphate may create a mechanical and chemical scaffold for new bone growth. In early stages of healing, small vessels may form and infiltrate large interstitial pores in a beta tricalcium phosphate mass. New osteoblasts may be recruited to the healing site. The osteoblasts may adhere to the surface of the beta tricalcium phosphate material. The osteoblasts may begin laying down collagenous osteoid bone matrix. Simultaneously, osteoclasts may break down the beta tricalcium phosphate material into basic chemical components. The basic chemical components may precipitate and crystallize in the osteoid bone matrix to mineralize the bone. As the healing process continues over a period of weeks and months, the beta tricalcium phosphate continues to resorb and the bone tissues become more organized. The bone tissues may eventually create lamellae or trabeculae. The resorption and remodeling process that takes place in the beta tricalcium phosphate scaffold may be substantially identical to the natural and ongoing process of bone healing.

FIG. 1 depicts an embodiment of spinal implant 20. Spinal implant 20 may include body 22 and insert 24. Body 22 may be formed of a material that provides spinal implant 20 with mechanical strength that is significantly greater than the strength of an intact, un-operated vertebral level. In some embodiments, body 22 may be formed from a block of beta tricalcium phosphate. Body 22 and/or insert 24 may be formed of or include a bio-absorbable material. In some embodiments, body 22 and/or insert 24 may be formed of or include metal (e.g., titanium and/or medical grade stainless steel), polymer, ceramic, bone or combinations thereof. In some embodiments, the metal may be a marker used to indicate a position of the spinal implant or a portion of the spinal implant. Polymers used in a spinal implant may include, but are not limited to, poly(L-lactide), poly(L,D/L-lactide), polyglycolide, poly(lactide-co-gylcolide), polycaprolactone, polydioxanone, polyetherether ketone, or combinations thereof.

Insert 24 may provide a scaffold that facilitates bone growth from adjacent vertebrae to the spinal implant. In some embodiments, insert 24 may be made of the same material as body 22. In some embodiments, insert 24 may be formed of a material different from the material used to form body 22. Insert 24 may include passageways 26. Passageways 26 may be filled with bone growth promoting material before spinal implant 20 is inserted between vertebrae. Body 22 may have mechanical strength that is significantly greater than the strength of insert 24. In some embodiments, insert may be formed of a porous and permeable material. The porous and permeable material may be, but is not limited to, ceramic (e.g., Cerasorb M), metal mesh, polymer, or a combination thereof.

During some procedures, a surgeon may decide to insert a body of an implant without using the insert. The surgeon may fill the opening where the insert would be positioned with bone growth promoting material. The bone growth promoting material may be, but is not limited to, autologous bone, allograft bone, xenograft bone, calcium phosphates, collagen, calcium sulfates, demineralized bone matrix, bone morphogenetic proteins, platelet derived growth factors, bone marrow aspirate, and/or blood. The material placed in the opening may be held in the opening by holding the material in with a finger during insertion of the spinal implant in the patient. In some embodiments, a bioabsorbable material (e.g., surgicel) may be used to hold the material placed in the opening during insertion of the spinal implant in the patient.

Body 22 may include cranial/caudal aspects (upper and lower surfaces), lateral aspects (side surfaces), and anterior/posterior aspects (front and back surfaces). Intersections of aspects of body 22 may be rounded so that the body has no sharp edges. In some embodiments, cranial/caudal aspects of body 22 may be substantially planar. In some embodiments, cranial/caudal aspects may include a curvature to conform to curvatures of cranial/caudal vertebrae surfaces that the body will contact. In some embodiments, anterior aspect 28 of body 22 may include a curvature to more closely conform to curvatures of adjacent vertebrae that the body is to be inserted between.

Figure 2:
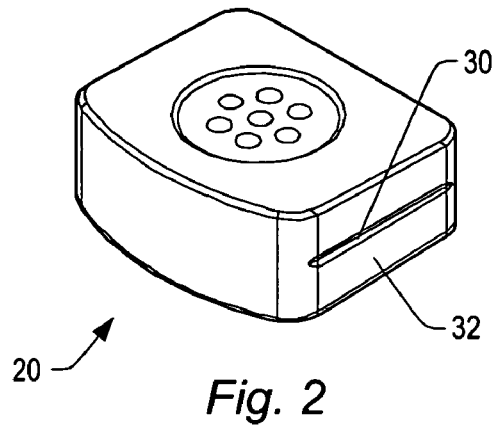
FIG. 2 depicts a perspective view of an embodiment of a spinal implant.

In some embodiments, a body of a spinal implant may include one or more protrusions and/or one or more grooves. In some embodiments, a protrusion on the body may engage a groove formed in a vertebra to position the body at a desired location during an insertion procedure. In some embodiments, an insertion tool may include a protrusion that engages a groove formed in the body so that the insertion tool is able to securely hold the body during insertion into a patient. FIG. 2 depicts an embodiment of spinal implant 20 with instrument groove 30 formed in lateral aspects 32.

Figure 3:
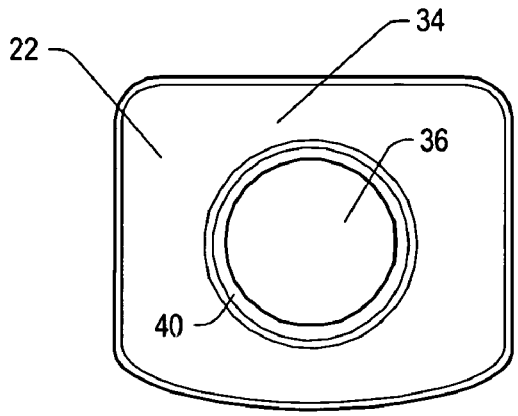
FIG. 3 depicts a top view of an embodiment of a body of a spinal implant.
Figure 4:
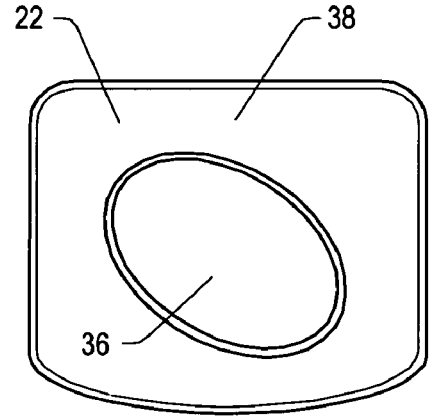
FIG. 4 depicts a bottom view of an embodiment of a body of a spinal implant.

FIG. 3 depicts cranial aspect 34 of an embodiment of body 22. Body 22 may include opening 36. Opening 36 may extend from the caudal aspect, through the body, to the cranial aspect. Opening 36 may be, but is not limited to being, circular, elliptical, oval, rectangular, or hexagonal. FIG. 4 depicts caudal aspect 38 of an embodiment of body 22 where the body includes elliptical opening 36. In some embodiments, the opening may have an irregular shape. Intersecting surfaces of the opening with the cranial aspect and the caudal aspect may be rounded so that the body has no sharp edges. In some embodiments, the opening may be sized so that an insert placed in the opening is inhibited from passing completely through the body. In the embodiment depicted in FIG. 3, surface 40 of body 22 that defines opening 36 is conically tapered so that a diameter of the opening at the cranial aspect is larger than a diameter of the opening at the caudal aspect. In some embodiments, the body may include a ledge or keyway that engages a portion of an insert to inhibit passage of the insert completely through the body.

Figure 5:
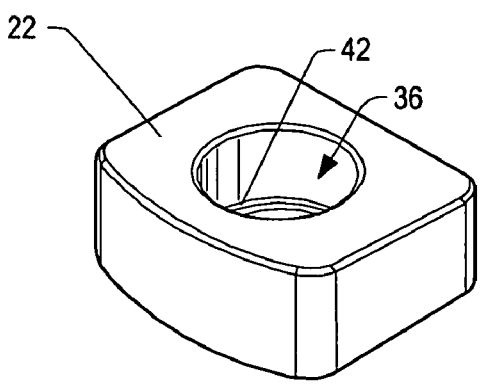
FIG. 5 depicts a perspective view of an embodiment of a body of a spinal implant.

FIG. 5 depicts an embodiment of body 22 that includes ledge 42. An insert positioned in the body may include a complementary ledge that contacts ledge 42 of body 22 to inhibit passage of the insert through opening 36 in the body. In some embodiments, a bottom surface of the insert may contact ledge 42 to inhibit passage of the insert through the body. Having body 22 with ledge 42 may allow for the formation of a spinal implant without the need to form tapered surfaces in the body of the spinal implant and/or the insert of the spinal implant.

Figure 6:
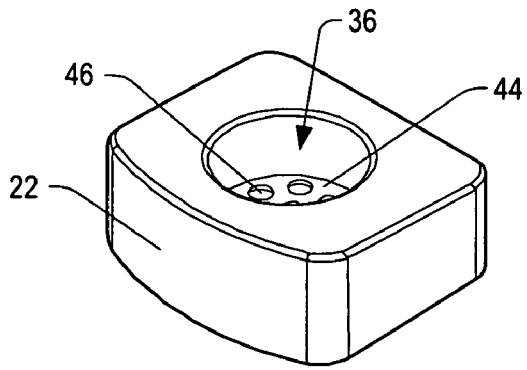
FIG. 6 depicts a perspective view of an embodiment of a body of a spinal implant.

FIG. 6 depicts an embodiment of body 22 that includes bottom surface 44. An insert may be positioned in opening 36 of body. Openings 46 in bottom surface 44 may allow for bone growth into and through body 22. In some embodiments, a bottom surface of the opening in the body may not include openings. The bottom surface may be formed of a permeable and porous material that will allow for bone growth into the body. Having a body with a bottom surface in the opening of the body may allow for the formation of a spinal implant without the need to form tapered surfaces in the body of the spinal implant and/or the insert of the spinal implant. In some embodiments, the insert may include a protrusion that engages a groove in the body to orient the insert relative to the body. In some embodiments, a wall defining the opening in the body may include a protrusion that fits in a groove in the body to orient the insert relative to the body. When the insert is oriented relative to the body, at least one passage through the insert may align with an opening in the bottom surface of the body.

In some embodiments of spinal implants, a body of the spinal implant may be formed from a block of beta tricalcium phosphate. An opening may be formed in the body using a drill or other boring machinery. If desired, a conical taper may be formed in the opening. In some embodiments, the conical taper may be from about 0.5° to about 45° relative to a center axis of the opening. In an embodiment, the conical taper may range from about 6° to about 12° relative to the center axis of the opening. Cranial and/or caudal aspects of the body may be planed to provide the spinal implant with a desired lordotic or kyphotic angle. In some embodiments, the cranial and/or caudal aspects may be shaped to more closely conform with the normal shape of vertebrae that that body is to be positioned between. During some insertion procedures, vertebral surfaces that the body is to contact may be chiseled or otherwise shaped so that such surfaces correspond to flat planar surfaces of the body. In some embodiments, an anterior aspect of the body may be shaped to more closely conform to the outer curvature of vertebrae that the body is to be positioned between.

Figure 7:
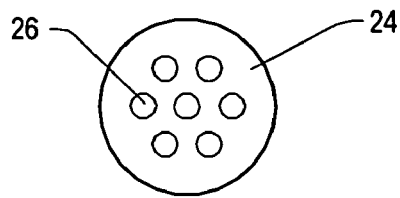
FIG. 7 depicts a top view of an embodiment of an insert.

FIG. 7 depicts a top view of an embodiment of insert 24. In some embodiments, insert 24 may be formed of a ceramic material (e.g., beta tricalcium phosphate). In some embodiments, insert 24 may be formed of allograft bone, demineralized bone, or xenograft bone. The insert may include a number of interconnected passages. The passages may facilitate bone growth from adjacent vertebrae that will fuse the vertebrae together. The passages may be passages formed (e.g., drilled) in the material of the insert, or the passages may be natural passages of the porous and permeable material of the insert.

Insert may include passageways 26. Passageways 26 may extend completely through insert 24 from the top surface to the bottom surface. Passageways may be pathways for bone growth that will fuse vertebrae together. Passageways may allow bone ingrowth into the insert to proceed at a faster rate than bone ingrowth into a body of the spinal implant. In some embodiments, passageways 26 are positioned in a pattern in insert. In some embodiments, passageways 26 may be substantially parallel to a central axis passing through the insert. In some embodiments, one or more passageways may be angled relative to a central axis passing through the insert. Passageways 26 may have sufficient size so that bone growth promoting material may be introduced into the passageways. In some embodiments, an effective diameter of passageways may be from about 0.1 mm to about 3 mm. The bone growth material may be, but is not limited to, autologous bone, allograft bone, xenograft bone, calcium phosphates, collagen, calcium sulfates, demineralized bone matrix, bone morphogenetic proteins, platelet derived growth factors, bone marrow aspirate, and/or blood.

Figure 8:
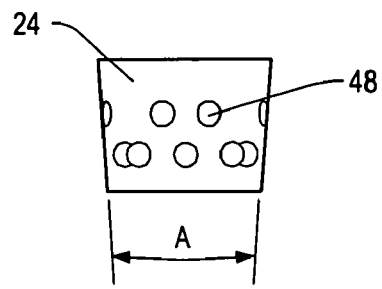
FIG. 8 depicts a side view of an embodiment of an insert.

FIG. 8 depicts a side view of an embodiment of insert 24. Insert may include passages 48. In some embodiments, passages 48 may be substantially the same size as passageways extending from the top surface of insert 24 to the bottom of the insert. In some embodiments, an effective diameter of passages 48 may be from about 0.1 mm to about 3 mm. In some embodiments, passages 48 through a side surface of insert 24 may extend completely through the insert. In some embodiments, passages 48 may not extend completely through insert 24. In some embodiments, passages 48 extending through a side of an insert may be substantially parallel to a bottom surface and/or top surface of insert 24. In some embodiments, passages 48 extending through a side of insert 24 may be angled relative to a top surface and/or a bottom surface of the insert.

As depicted in FIG. 8, insert may be tapered at angle A. The tapered surface of insert may substantially complement a tapered surface defining an opening in a body of a spinal implant. Angle A may be from about 1° to about 30°. The complementing tapers of insert 24 and the body of a spinal implant may inhibit complete passage of the insert through the body. The complementing tapers may properly position the insert relative to the body when the insert is fully positioned in the body.

Figure 9:
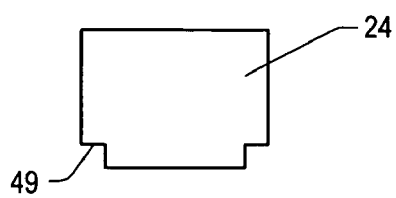
FIG. 9 depicts a side view of an embodiment of an insert.

FIG. 9 depicts a side view of an embodiment of insert 24. Insert 24 includes ledge 49. Ledge 49 may complement ledge 42 (depicted in FIG. 5) to inhibit passage of insert 24 through the body of the spinal implant when the insert is positioned in the body. Insert 24 may be made of a permeable and porous material.

Figure 10:
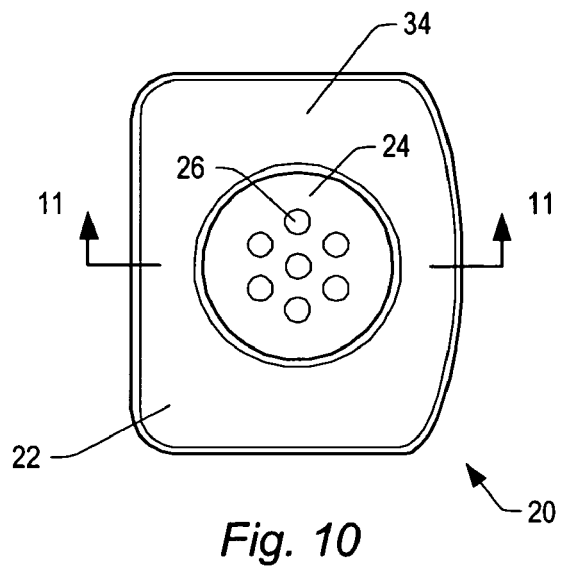
FIG. 10 depicts a top view of a spinal implant embodiment.
Figure 11:
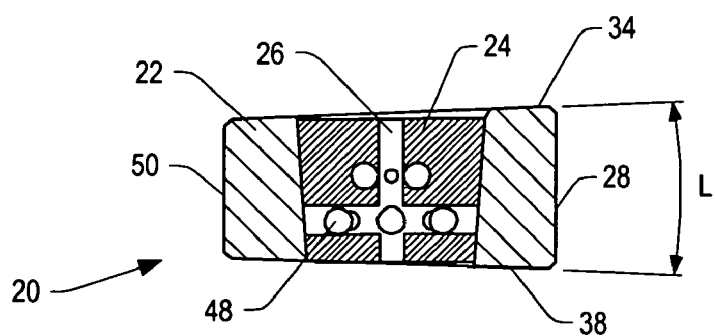
FIG. 11 depicts a cross-sectional representation of an embodiment of a spinal implant, the cross section taken substantially along line 11-11 of FIG. 10.

FIG. 10 depicts a view of cranial aspect 34 of an embodiment of spinal implant 20 when insert 24 is fully inserted in body 22. FIG. 11 depicts a cross-sectional representation of spinal implant 20. Passages 48 through a side surface of insert 24 may intersect with one or more passageways 26 extending from the top surface of the insert to the bottom surface of the insert. After insertion of spinal implant 20 in a disc space between vertebrae, bone growth may occur in passages 48 and passageways 26. Bone growth in passages 48 may secure the spinal implant within the disc space without the need for bone growth to be complete from a caudal aspect of the spinal implant to a cranial aspect of the spinal implant.

As shown in FIG. 11, cranial aspect 34 and caudal aspect 38 of body 22 may be at an angle L relative to each other. The angle L is the lordotic angle if the height of the body adjacent anterior aspect 28 is greater than the height of the body adjacent posterior aspect 50. The angle L is the kyphotic angle if the posterior height of the body is greater than the anterior height of the body.

A body and/or an insert of a spinal implant may be made of beta tricalcium phosphate. The spinal implant may have greater strength than the strength of an intact, un-operated on vertebral level. Tests were performed on 5 mm×14 mm×12 mm beta tricalcium phosphate spinal implants with inserts positioned in openings of the body. The tests were compressive tests to failure of the spinal implants. A first test group of six spinal implants had no visible defects. The average peak load at failure for the first test group was 8260 N. The smallest peak load was 5760 N for one specimen.

Figure 12:
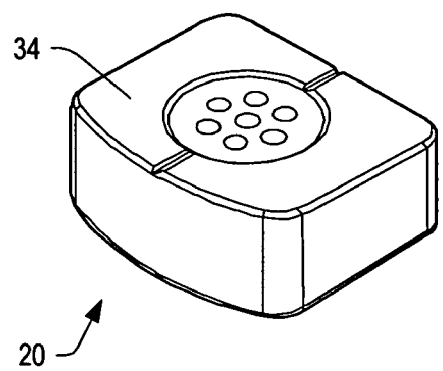
FIG. 12 depicts a perspective view of an embodiment of a spinal implant.

A second test group of six spinal implants had anterior/posterior defects formed in cranial/caudal aspects. FIG. 12 depicts a perspective view of spinal implant 20 with anterior/posterior defects formed in cranial aspect 34 and the caudal aspect. The defects were 0.5 mm V-shaped notches formed by a router. The average peak load at failure for the second test group was 7150 N. The smallest peak load was 5160 N for one specimen.

The mean static compressive strength of a beta tricalcium phosphate spinal implant without a noticeable defect was 8260 N. The mean static compressive strength of a beta tricalcium phosphate spinal implant with a 0.5 mm V-shaped with an anterior/posterior defect formed in cranial/caudal aspects of the block was 7150 N, which is not significantly different than the compressive strength for a spinal implant without a defect. The mean static compressive strength of an intact, un-operated cervical vertebral level is about 1600 N. The compressive strength of the tested beta tricalcium phosphate spinal implants provided a safety factor of greater than 3 for all spinal implants tested relative to the strength of an intact cervical vertebral level. If a beta tricalcium phosphate spinal implant was used, a compressive failure would be expected to involve the vertebral body and/or soft tissue structures rather than the spinal implant.

Figure 13:
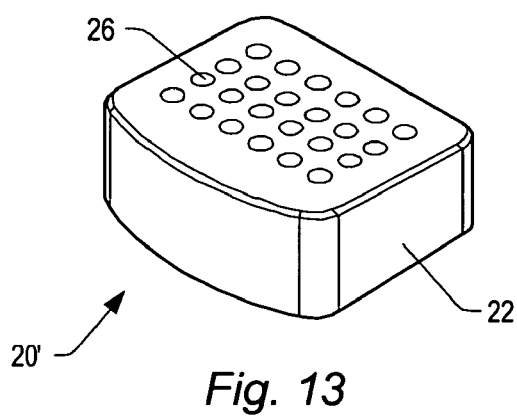
FIG. 13 depicts an embodiment of a spinal implant.

In some embodiments, a spinal implant may be formed without an insert. The spinal implant may be made from beta tricalcium phosphate. FIG. 13 depicts an embodiment of spinal implant 20'. Spinal implant 20' may include body 22 and passageways 26. Passageways 26 may extend completely through body 22. In some embodiments, one or more passages may be formed in side surfaces of the body. The passage or passages may intersect with one or more of the passageways through the spinal implant.

Figure 14:
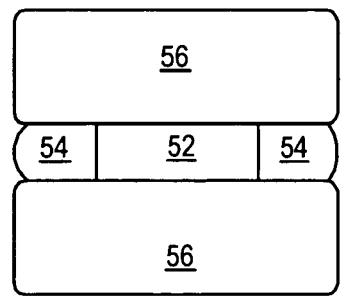
FIG. 14 depicts a representation of a vertebral level after a discectomy.

A discectomy may be performed to form a disc space for a spinal implant. A portion or all of an intervertebral disc may be removed during the discectomy. FIG. 14 depicts a representation of disc space 52 formed in intervertebral disc 54. A distractor or distractors may be used to establish and maintain a separation distance between vertebrae 56. The separation distance may be slightly smaller than the largest height of an implant that is to be inserted into the prepared disc space. Vertebral endplates that the spinal implant is to be positioned adjacent to may be cleaned of any residual disc material and any osteophytes may be removed. The vertebral surfaces may be treated using a chisel, dibbler, or other instrument so that the body's bone healing process will be activated at the location where the spinal implant is to be inserted.

An insert may be prepared. Solid or thick bone growth promoting material (e.g., bone chips) may be introduced into passageways of the insert. The bone growth promoting material may be pressed into the passageways of the insert. The insert may be soaked in a solution. The solution may be blood obtained from the patient, bone marrow aspirate, and/or a solution containing bone growth materials (e.g., bone morphogenetic proteins and/or platelet derived growth factors). A portion of the solution may be absorbed into the passageways of the insert.

Figure 15:
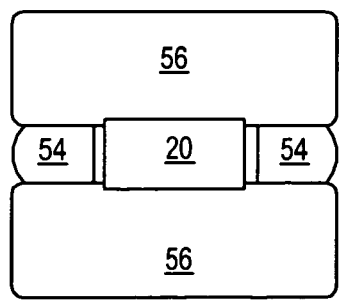
FIG. 15 depicts a representation of a spinal implant embodiment inserted in a disc space between vertebrae.
Figure 16:
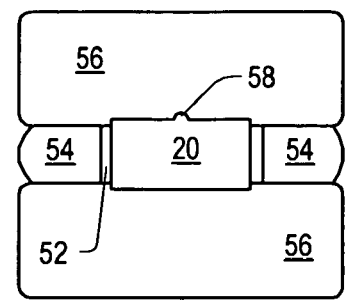
FIG. 16 depicts a representation of a spinal implant embodiment inserted in a disc space between vertebrae.

The insert may be placed in a body to form a spinal implant. The spinal implant may be grasped using an insertion tool. In some embodiments, the insertion tool may be forceps. The spinal implant may be positioned in the prepared disc space, and the insertion tool may be removed. If needed, a tamp may be used to drive the spinal implant into the disc space. FIG. 15 depicts a representation of spinal implant 20 positioned between vertebrae 56. Bone growth promoting material may be inserted in space between spinal implant 20 and intervertebral disc 54 if desired. FIG. 16 depicts a representation of spinal implant 20 positioned between vertebrae 56. Spinal implant 20 includes guide 58 that fits in a groove formed in a vertebra. Guide 58 may position spinal implant at a desired location in disc space 52.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A human intervertebral fusion spacer, comprising:
    a body comprising a block of bioabsorbable material selected to promote bone growth and having a compressive strength at least as great as the compressive strength of an intact vertebra, the body defining a central opening fully open at and extending from a cranial aspect of the body towards a caudal aspect of the body and fully surrounded on lateral, anterior and posterior sides by the body, wherein the body is shaped to conform to a general shape of outer surfaces of a vertebra; and
    an insert comprising a single solid block of bioabsorbable material having a shape and length complementary to the shape and length of the opening in the body,
        wherein the body has a mechanical crush resistance that is greater than the mechanical crush resistance of the insert,
        wherein the insert has a plurality of man-made passageways extending from a top surface of the insert to a bottom surface of the insert,
        wherein the insert has at least one man-made passage that extends through a side surface of the insert and intersects with one or more of the plurality of man-made passageways,
        wherein the plurality of man-made passageways and the at least one man-made passage are sized to promote bone growth that fuses adjacent vertebrae together when the insert is positioned in the opening of the body and the insert and the body are placed between the adjacent vertebrae and are sized to allow bone growth promoting material to be inserted in the passageways, wherein the body is shaped so that a portion of the opening open to the cranial aspect of the body is sufficiently large to receive the insert and a portion the opening more proximate to the caudal aspect of the body is smaller than a cross-section of the insert to inhibit the insert from passing out the opening through the caudal aspect of the body,
        wherein the plurality of man-made passageways and the at least one man-made passage are drilled through-holes containing a bone growth promoting material therein.

2. The human intervertebral fusion spacer of claim 1, wherein the insert comprises a permeable and porous material.

3. The human intervertebral fusion spacer of claim 1, wherein the spacer is configured such that bone ingrowth into the insert occurs at a faster rate than bone ingrowth into the body.

4. The human intervertebral fusion spacer of claim 1, wherein the body has a bottom surface and wherein when the insert is oriented relative to the body, at least one of the plurality of man-made passageways of the insert aligns with a hole in the bottom surface of the body.

5. The human intervertebral fusion spacer of claim 1, wherein the insert comprises a first man-made passage and a second man-made passage, and wherein the first man-made passage is nonparallel relative to the second man-made passage.

6. The human intervertebral fusion spacer of claim 1, wherein the insert comprises a first man-made passage and a second man-made passage, wherein the first man-Made passage is nonparallel relative to the second man-made passage, and wherein the first man-made passage intersects the second man-made passage.

7. The human intervertebral fusion spacer of claim 1, wherein an upper surface of the body is angled relative to a lower surface of the body to establish a desired amount of lordosis between the human vertebrae.

8. The human intervertebral fusion spacer of claim 1, wherein the body comprises a guide configured to mate to a corresponding guide formed in a vertebra to guide the body during insertion.

9. The human intervertebral fusion spacer of claim 1, wherein the body is sized to fit between cervical vertebrae.

10. The human intervertebral fusion spacer of claim 1, wherein the body is sized to fit between lumbar vertebrae.

11. The human intervertebral fusion spacer of claim 1, wherein the insert is made of same material as the body.

12. The human intervertebral fusion spacer of claim 1, wherein the insert is made of a material different from the block of material used to form the body.

13. The human intervertebral fusion spacer of claim 1, wherein the interior of the body is conically tapered in which a first diameter of the opening at the cranial aspect of the body is larger than a second diameter of the opening at the caudal aspect of the body.

14. The human intervertebral fusion spacer of claim 1, wherein the interior of the body comprises a ledge or keyway for engaging a portion of the insert at the second end of the body when the insert is positioned in the opening of the body.

15. The human intervertebral fusion spacer of claim 14, wherein the insert comprises a feature that complements the ledge or keyway of the body.

16. The human intervertebral fusion spacer of claim 1, wherein the exterior of the body comprises one or more protrusions positioned to engage a bottom or top portion of the vertebrae.

17. The human intervertebral fusion spacer of claim 1, wherein the exterior of the body comprises one or more grooves for engaging a portion of a tool.

18. The human intervertebral fusion spacer of claim 1, wherein at least one of the plurality of man-made passageways extending from the top surface of the insert to the bottom surface of the insert is sized to receive the bone growth promoting material.

19. The human intervertebral fusion spacer of claim 1, wherein the at least one man-made passage extending through the side surface of the insert is sized to receive the bone growth promoting material.

20. The human intervertebral fusion spacer of claim 1, wherein the plurality of man-made passageways and the at least one man-made passageway have a diameter of 0.1 mm to 0.3 mm.

* * * * *